United States Patent [19]
Narciso, Jr.

[11] Patent Number: 5,456,661
[45] Date of Patent: Oct. 10, 1995

[54] CATHETER WITH THERMALLY STABLE BALLOON

[75] Inventor: Hugh L. Narciso, Jr., Santa Barbara, Calif.

[73] Assignee: PDT Cardiovascular, Santa Barbara, Calif.

[21] Appl. No.: 221,828

[22] Filed: Mar. 31, 1994

[51] Int. Cl.$^6$ .......................... A61N 1/30; A61M 29/00; A61M 31/00; A61B 17/36
[52] U.S. Cl. ................ 604/20; 604/49; 604/96; 606/15
[58] Field of Search ................ 606/13–17; 604/49–50, 604/20, 96

[56] References Cited

U.S. PATENT DOCUMENTS

| | | | |
|---|---|---|---|
| 4,003,382 | 1/1977 | Dyke | 604/96 X |
| 4,685,447 | 8/1987 | Iversen et al. | 604/96 X |
| 5,292,320 | 3/1994 | Brown et al. | 606/15 |
| 5,312,392 | 5/1994 | Hofstetter et al. | 606/2 |
| 5,320,617 | 6/1994 | Leach | 606/15 |

Primary Examiner—John D. Yasko
Assistant Examiner—Adam J. Cermak
Attorney, Agent, or Firm—Michael G. Petit

[57] ABSTRACT

An intraluminal catheter with an inflatable fluoropolymer balloon is described. The catheter, generally comprising an elongate body portion dimensioned to be inserted within a body lumen, has a fluoropolymer inflatable member affixed to the outer surface and coaxial with the body portion. An inflation lumen provides fluid communication between the interior portion of the inflatable member and a source of inflation fluid. The catheter preferably has means thereon for conducting light to a portion of the catheter underlying the inflatable member. The fluoropolymer inflatable member can be positioned within a lumen of the body and inflated with a transparent fluid. The non-blocking (non-sticky) property of fluoropolymer resins permits easy inflation while the transparency and thermal stability permit the conduction of high power illuminating light from a source within the catheter through the fluoropolymer wall of the inflatable member to the surrounding tissue. The fluoropolymer wall of the balloon maintains its' structural integrity upon heating by the transmitted light thus permitting the delivery of higher power levels of illumination to surrounding tissue.

6 Claims, 3 Drawing Sheets

CATHETER WITH THERMALLY STABLE BALLOON

BACKGROUND OF THE INVENTION

1. Field of the Invention

This invention is a catheter which includes an inflatable balloon fabricated from fluoropolymer resins. The catheter is useful in the fields of cardiovascular medicine, photodynamic therapy, cancer treatment, benign prostatic hypertrophy, neurovascular medicine, diagnostic medicine and other fields which require the use of a balloon catheter.

2. Prior Art

Percutaneous Transluminal Coronary Angioplasty (PTCA) is performed more than 400,000 times per year in the United States alone to treat the disease which is the leading cause of death, cardiovascular disease. In addition to PTCA, more than 250,000 Percutaneous Transluminal Angioplasties (PTA) are performed on the peripheral vasculature, again per year in the U.S. A treatment for cancer, the second leading killer in the U.S. (over 500,000 deaths per year), includes Photodynamic Therapy (PDT) of the gastrointestinal tract, urologic tract, pulmonary tree, and neurologic system. Photoatherolytic (PAL) Therapy has shown some early promise for the treatment of atherosclerosis and restenosis, and has been proposed for the Photoinhibition Therapy for Hyperplasia (PITH). Treatments of such widespread maladies such as Benign Prostatic Hypertrophy (BPH) and occlusive cancer of the esophagus include balloon dilatation, Interstitial Laser Photocoagulation (ILP), Laser-Induced Hyperthermia (LIH),Ultrasound Induced Hyperthermia, and Radio-Frequency Hyperthermia (RFH). The unifying parameter among the treatments for all of the above diseases is the use of a balloon catheter. The utility of the balloon catheter varies from dilatation to partial occlusion to total occlusion to short and long term patency (perfusion balloon) to local drug delivery to local device deployment to heat delivery to light delivery to various diagnostic applications to imaging to positioning to on line thermal, optical, or pharmacology dosimetry.

Angioplasty balloon catheters such as that described by Gruntzig, et at, in U.S. Pat. No. 4,195,637 and other prior art catheters adapted for the myriad of applications and utilities listed above are commonly fabricated from polyurethane, polyethylene, polyethylene terephthalate, polyethylene blends, polyolefin blends, nylon, polyamide, silicone, latex, etc. Materials such as these exhibit different qualities such as strength, biocompatability, compliance, and manufacturability, which are required for various medical procedures. As newer medical modalities are tested and proven, new demands are place on the qualities of the treatment balloon catheter device, such as optical clarity and thermal stability. Many of the materials stated above have a plurality of the requirements, but none have all, both old and new, requirements.

In cardiovascular medicine, balloon catheters are used for angioplasty (U.S. Pat. No. 4,323,071 Simpson), both in the coronary arteries and the peripheral vasculature which includes arteries of the arms, legs, renal system, and the cerebral arteries. Balloon catheters s are also used for photo-medicine in the treatment of cardiovascular disease (CVD) in procedures such as Photodynamic Therapy (PDT), Photoatherolytic Therapy, Photochemical Therapy, and Photo-Welding, either photothermal or photochemical, of an anastomosis (U.S. Pat. No. 5,169,395 to Narciso, Jr.). Balloons are also used for atherectomy/atherotomy for positioning and occlusion while they are also used in the deployment of various types of stents. Treatments for CVD which require balloon catheters outside of the treatment of atherosclerosis and restenosis include valvuloplasty and various electrophysiology procedures.

Cancer, the second leading cause of death in the U.S., can also be treated with procedures requiring balloon catheters. PDT is a very promising modality for this application (U.S. Pat. No. 4,932,934 Dougherty). PDT will compete directly with present laser therapies such as photocoagulation or ablative therapies to treat obstructive cancers. Another treatment being investigated is the use of localized heating (Hyperthermia) to selectively neerose cancer cells. The heat can be produced with a light source such as a laser or a non-light source such as a radio-frequency (RF) source, a microwave source, or an ultrasonic source.

Benign Prostatic Hypertrophy (BPH) is a non-cancerous hyperproliferative disease which invades the prostate of 80% of men by the time they reach the age of 80 years old. Various procedures are available for the treatment of BPH which include Hyperthermia (laser, RF, microwave, ultrasound), PDT, balloon dilation surgery and ablative procedures; all having varying success rates.

The forgoing materials have been successfully employed for catheters for many years. As mentioned above, new procedures such as transluminal hyperthermia require a balloon material which is transparent to the wavelengths of light employed for inducing hyperthermia and able to withstand high temperatures. In transluminal hyperthermia, a catheter which incorporates a balloon is inserted into a body lumen. The balloon, located near the distal tip, is inflated. A light diffuser tip within the catheter directs light from an external source through the wall of the balloon to penetrate the surrounding tissue. Currently employed elastomers for balloon fabrication are unable to withstand high temperature generated during such applications.

Additionally, when a catheter is stored for a long time with a balloon in a collapsed position, the elastomer comprising the balloon may stick to itself making inflation difficult. It is particularly desirable to provide a catheter having an inflatable balloon which employs a wall material which does not stick to itself. TEFLON® brand of fluoropolymer resins, which is not currently used as a wall material in such catheter balloons, has the desirable properties of high thermal stability, light transparency and a non-blocking (non-sticky) surface.

Teflon® is a DuPont registered trademark for a family of fluoropolymer resins. This family of fluoropolymers include: polytetrafluoroethylene (fluoropolymer), fluorinated ethylene-propylene (FEP), perfluoroalkoxy (PFA), and ethylene tetrafluoroethylene (ETFE). TEFLON® is characterized by its' extended thermal properties, resistance to virtually all chemicals, low coefficient of friction, lubriciousness, and relative clarity. Both FEP and PFA are melt-extrudable resins with the clarity required for optical applications and extended thermal characteristics inherent in all forms of TEFLON® brand of fluoropolymer resin. Both exhibit tensile strengths in the range of 4,000 psi with ultimate elongation percentage of 300–500 and a coefficient of friction in the range of 0.20–0.25. The flexural modulous is 95–105×10 psi and the continuous operating temperature is 204 degrees C. for FEP and over 260 degrees C. for PFA. The melting point for FEP is 253–282 degrees C. and 302–310 degrees C. for PFA. These properties make FEP and PFA excellent materials for fabricating a high temperature, chemical resistant, strong, optically clear, compliant easily manufactured balloon.

The greatest need for all of the applications previously listed is the ability of the walls of the balloon portion of the balloon catheter to withstand high thermal conditions. Regardless of the heating source (i.e. laser, arc lamp, LED, RF, microwave, or ultrasound), the device must not fail. Medical light and heat treatments require a dependable thermally stable balloon device. A balloon catheter meeting these requirements is described below.

SUMMARY OF THE INVENTION

It is the object of the present invention to provide a balloon catheter for insertion into a body lumen.

It is a further object of the present invention to provide a catheter with an inflatable balloon device which can withstand relative high temperatures when compared with elastomers currently used is such applications.

It is a further object of the present invention to provide a catheter having a inflatable balloon in which the walls of the balloon are transparent.

It is a further object of the present invention to provide a balloon catheter useful for a variety of medical procedures.

It is a further object of the present invention to provide a catheter having an inflatable balloon thereon where the balloon is fabricated from an elastomer that will not stick to itself.

It is a further object of the present invention to provide a catheter that comprises a material which is highly lubricious.

It is a further object of the present invention to provide a balloon device which can be easily bonded to a catheter designed for thermal, optical or other various therapies.

The present invention solves the problems of the devices mentioned as prior art. Other objects and further scope and applicability of the present invention will become apparent to one skilled in the art from the detailed description to follow taken in conjunction with the accompanying drawing.

BRIEF DESCRIPTIONS OF THE DRAWINGS

DESCRIPTION OF THE PREFERRED EMBODIMENT

Figure 1:
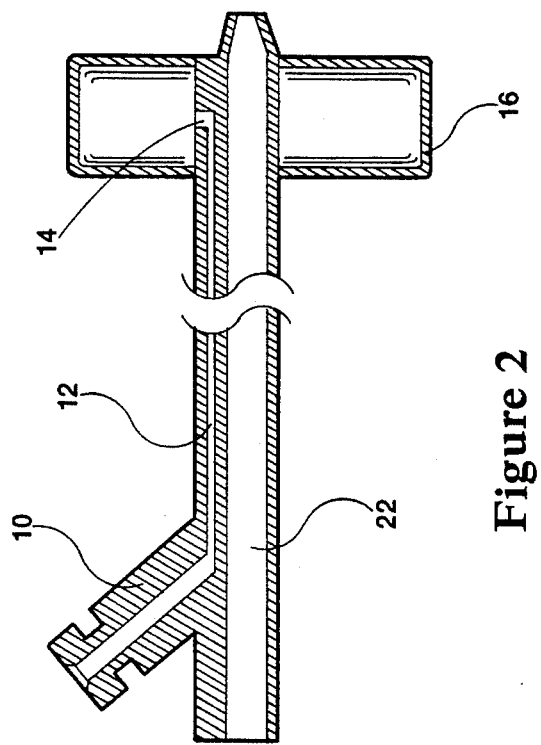
FIG. 1 is a cross-sectional view of a prior art balloon catheter.
Figure 2:
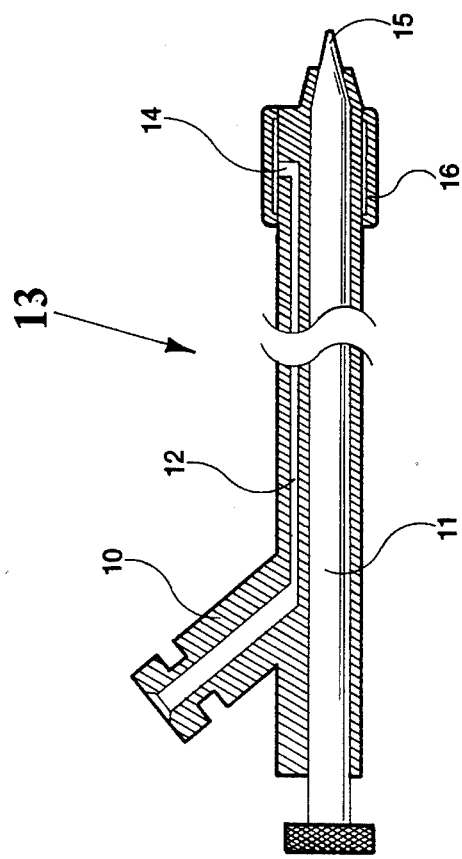
FIG. 2 shows the balloon catheter of FIG. 1 with the balloon inflated.

FIGS. 1 and 2 are cross-sectional longitudinal views of a typical balloon catheter according to the prior art. The balloon catheter, generally indicated at the numeral 13, has a proximal end 17 and a distal end 15 and a body portion 18 therebetween. The body portion 18 has a guidewire lumen 22 (FIG. 2) coextensive therewith dimensioned to accommodate a guidewire 11. An inflatable member such as a balloon 16 encircles the distal end of the catheter. A fill port 10 is in fluid communication with the interior of the balloon 14 by means of an inflation lumen 12. In operation, the guidewire 11 is advanced through the lumen of a tubular tissue until the guidewire tip underlies a target. The catheter 13 is slid over the guidewire and advanced until the balloon 16 underlies the target and the balloon 16 is inflated as shown in FIG. 2. The walls 16 of the balloon may press against the target tissue (not shown) and/or occlude the lumen (not shown).

Figure 3:
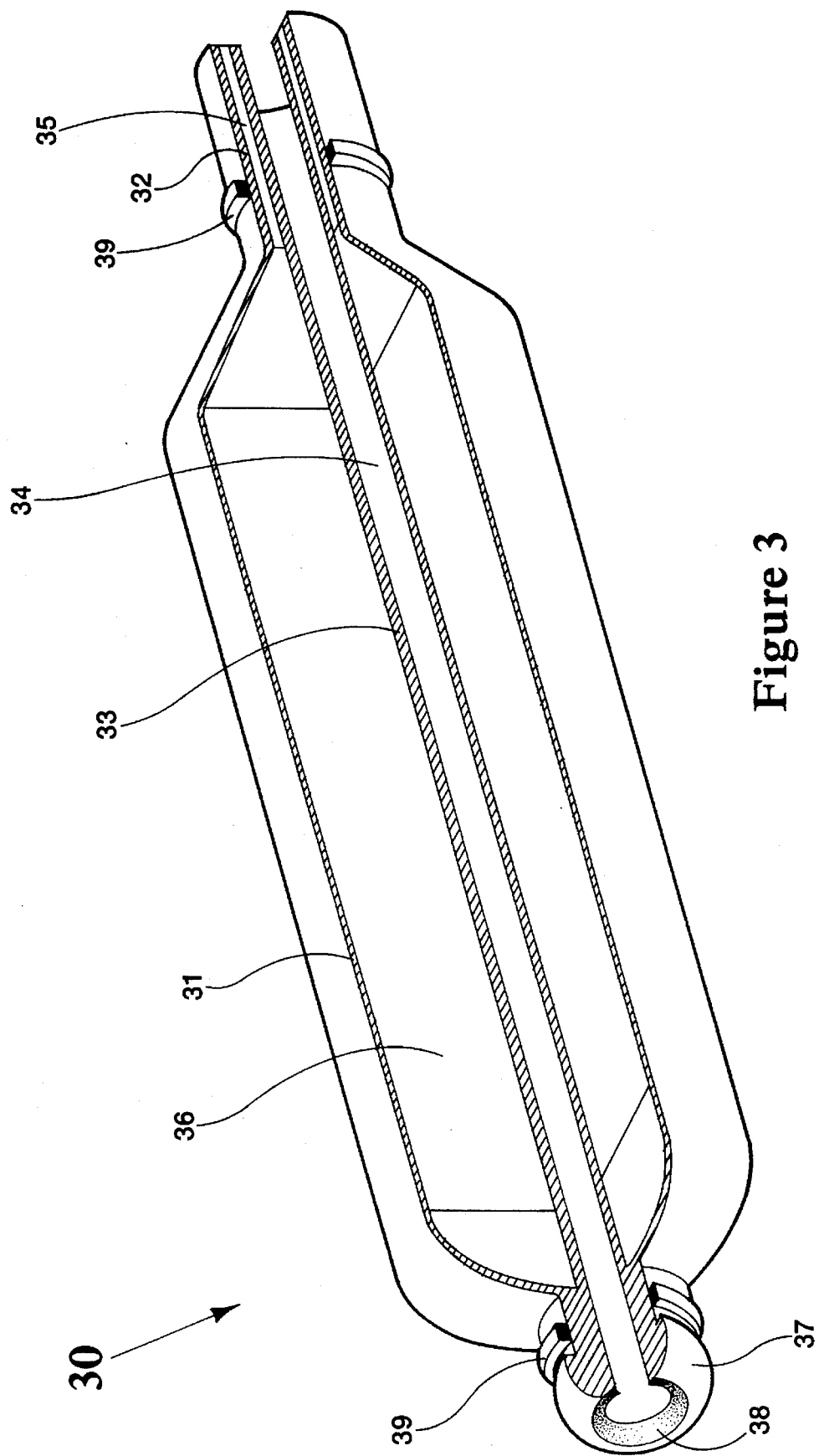
FIG. 3 is an isometric view with a quarter section removed of a typical TEFLON® Balloon catheter of a preferred embodiment of the present invention.

FIG. 3 is an illustration of the preferred embodiment of the distal end of a TEFLON brand of fluoropolymer resin balloon catheter of the present invention generally indicated at 30. The fluoropolymer balloon 31 is affixed to the fluoropolymer outer sheath 32 by the application of heat and pressure thereto as is well known in the manufacturing arts. The fluoropolymer inner tube 33 houses the guidewire lumen 34 which is a dedicated channel for a guidewire (not shown) or it may also be used for providing fluid, gaseous or liquid from an external port to the treatment site. The space between the outer sheath 32 and the inner tube 33 is referred to as the inflation/deflation channel 35 or, in the alternative, as the inflation lumen, which provides access for the inflation medium 36 to fill the balloon 31. The distal tip 37 is rounded for easy atraumatic introduction of the device into a body lumen and incorporates a funnel introducing port 38 which abuts the guidewire lumen 34 and facilitates the threading of the distal tip over a guidewire (not shown). Marker bands 39 are located distal and proximal to the balloon for identification and positioning under x-ray fluoroscopy.

Figure 4:
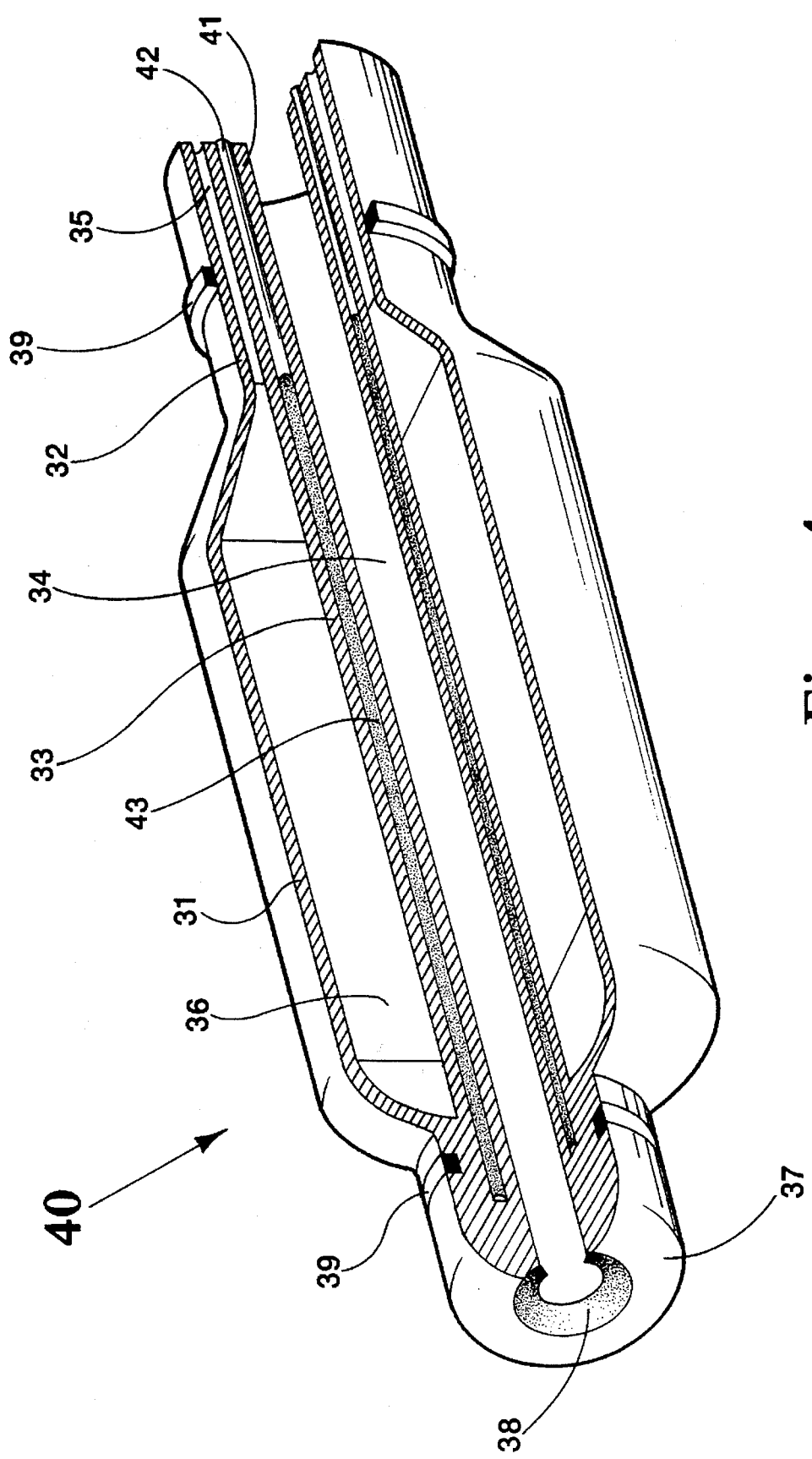
FIG. 4 is an isometric view of a preferred embodiment of a light diffusing fluoropolymer balloon catheter according to the present invention with a quarter section removed.

FIG. 4 is an illustration of a second preferred embodiment of the present invention generally indicated a 40. The balloon components and the tip configuration are identical to those of FIG. 3, but light delivery and diffusing elements have been added for light and/or heat applications of the device. The fluoropolymer balloon 31 is affixed to the catheter body 32. The inflation medium 36 is supplied via the inflation/deflation channel 35 and is retained between the balloon 31 and the inner tube 33. A central lumen 34 which enables the delivery of a fluid or guidewire (not shown) to the distal tip terminates at the funnel introducing port 38. Marker s bands 39 are placed distal and proximal to the balloon 31 for identification and positioning under x-ray fluoroscopy. Positioned between the inner tube 33 and the central lumen 34 is a cylindrical light diffusing tip 43. The light conducting element consists of an inner sheath 41 which provides support to an array of optical fibers 42 which terminate in a cylindrical diffuser tip 43. The diffusion tip preferably consists of a transparent elastomer such as silicone with light scattering centers such as alumina interspersed therein. The optical fibers 42 conduct light form an external light source (not shown) to the cylindrical diffusing tip 43 and both are contained between the inner sheath 41 and inner lumen 33.

Depending on the application, the inflated balloon diameter can be as small as 1.0 mm or as large as 20 mm. The body of the catheter will be in proportion to the balloon section varying from sub-millimeter diameters to multiple millimeters diameter. The open central channel, if so equipped, can be as small as 0.010 in. or larger than 0.050 in. The wall thickness of the balloon may be as little as 0.1 mm which, in a deflated condition, provides an extremely low profile for insertion into, for example, a blood vessel.

Local drug delivery is a field which is in its infancy. As new pharmacokinetic therapies are developed for diseases such as CVD, cancer, BPH, etc. local delivery devices will increase in importance. Balloon types of delivery devices such as coated balloons, porous balloons, and dual-balloon catheters (the lumen being treated is occluded proximally and distally to the localized area where the drug is delivered) will need to be developed.

Diagnostic applications are being developed to take more of a prospective view to medicine. Balloon catheters are presently used for angioscopy, intravascular ultrasound imaging, angiography, and fluorescence imaging. Fluorescence imaging can be enhanced by the use of a fluorophore, chromophore, or photosensitizer.

The above is a detailed description of a preferred embodiment of the present invention. It is recognized that departures from the disclosed embodiment may be within the scope of this invention an that obvious modifications will occur to a person skilled in the art. The full scope of the invention is set out in the claims that follow and their equivalents, Accordingly, the claims and specification should not be construed to unduly narrow the full scope of protection to which the invention is entitled.

What I claim is:

1. A balloon catheter comprising an elongate tubular member having a proximal end and a distal end and a body portion therebetween and an inflation lumen coextensive with at least a portion of said body portion and an inflatable member having a wall consisting of a fluoropolymer resin, at least a portion of said wall being affixed externally to said body portion to provide a fluid-tight compartment therebetween and wherein said inflation lumen is in fluid communication with said fluid-tight compartment.

2. A method for performing a medical procedure comprising the insertion of a balloon catheter according to claim 1 into a tubular tissue within the body of a patient.

3. The method of claim 2 wherein said medical procedure comprises the treatment of Benign Prostatic Hypertrophy.

4. The method of claim 3 wherein said treatment comprises hyperthermia.

5. The method of claim 3 wherein said treatment comprises photodynamic therapy.

6. The balloon catheter according to claim 1 further comprising a means for conducting light from said proximal end of said body portion to a portion of the catheter underlying said inflatable member and wherein said means for conducting light further comprises a diffuser tip underlying said wall of said inflatable member and wherein said fluoropolymer resin is substantially optically transparent.

* * * * *